United States Patent
Koo

(10) Patent No.: US 10,787,637 B2
(45) Date of Patent: Sep. 29, 2020

(54) CONTINUOUS FERMENTER FOR SEQUENTIAL FERMENTATION OF HEXOSE-PENTOSE

(71) Applicant: SK Innovation Co., Ltd., Seoul (KR)

(72) Inventor: Min Su Koo, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 241 days.

(21) Appl. No.: 15/351,866

(22) Filed: Nov. 15, 2016

(65) Prior Publication Data
US 2017/0145375 A1 May 25, 2017

(30) Foreign Application Priority Data
Nov. 19, 2015 (KR) .................. 10-2015-0162793

(51) Int. Cl.
| | | |
|---|---|---|
| *C12M 1/00* | (2006.01) | |
| *C12M 1/12* | (2006.01) | |
| *C12M 1/02* | (2006.01) | |
| *C12M 1/06* | (2006.01) | |

(52) U.S. Cl.
CPC .......... *C12M 43/02* (2013.01); *C12M 23/04* (2013.01); *C12M 41/18* (2013.01); *C12M 27/06* (2013.01); *C12M 41/22* (2013.01)

(58) Field of Classification Search
None
See application file for complete search history.

(56) References Cited

U.S. PATENT DOCUMENTS

| | | | |
|---|---|---|---|
| 4,654,308 A * | 3/1987 | Safi .................. | C02F 3/2806 312/209 |
| 7,942,011 B2 | 5/2011 | Forkosh | |
| 9,856,601 B2 | 1/2018 | Stromberg | |
| 9,976,161 B2 | 5/2018 | Kim et al. | |
| 2016/0152934 A1 | 6/2016 | Shin et al. | |

FOREIGN PATENT DOCUMENTS

| | | | |
|---|---|---|---|
| JP | 2009296983 A | | 12/2009 |
| KR | 101261560 B1 | | 5/2013 |
| KR | 1020130046382 A | | 5/2013 |
| KR | 101366379 B1 | | 2/2014 |
| KR | 1020150047576 A | | 5/2015 |
| KR | 1020150117599 | | 10/2015 |
| WO | WO 2013/062372 | * | 5/2013 |

OTHER PUBLICATIONS

Swain et al. "Improved conversion of rice straw to ethanol and xylitol by combination of moderate temperature ammonia pretreatment and sequential fermentation using Candida tropicalis". Industrial Crops and Products 77 (2015) pp. 1039-1046; available on line Oct. 22, 2015.*

Kumar et al.; "Recent Advances in Production of Bioethanol from Lignocellulosic Biomass"; Chem. Eng. Technol.; 2009; pp. 517-526; vol. 32:4.

* cited by examiner

*Primary Examiner* — Vera Afremova
(74) *Attorney, Agent, or Firm* — The Webb Law Firm

(57) ABSTRACT

Discloses is a continuous fermenter for sequential fermentation of hexose and pentose which includes (a) a hexose fermenter equipped with a saccharified solution supply unit containing hexose, pentose and lignin, a plurality of trays closing at least half of the diameter of the fermenter, impellers disposed on each of the trays, an impeller driving unit, a lignin discharge unit disposed at the bottom of the fermenter, a fermented solution discharge unit, and a temperature control jacket; and (b) a pentose fermenter equipped with a fermented solution supply unit for supplying the fermented solution discharged from the hexose fermenter, a plurality of trays closing at least half of the diameter of the fermenter, impellers disposed on each of the trays, an impeller driving unit, a lignin discharge unit disposed at the bottom of the fermenter, a fermented solution discharge unit, and a temperature control jacket.

6 Claims, 1 Drawing Sheet

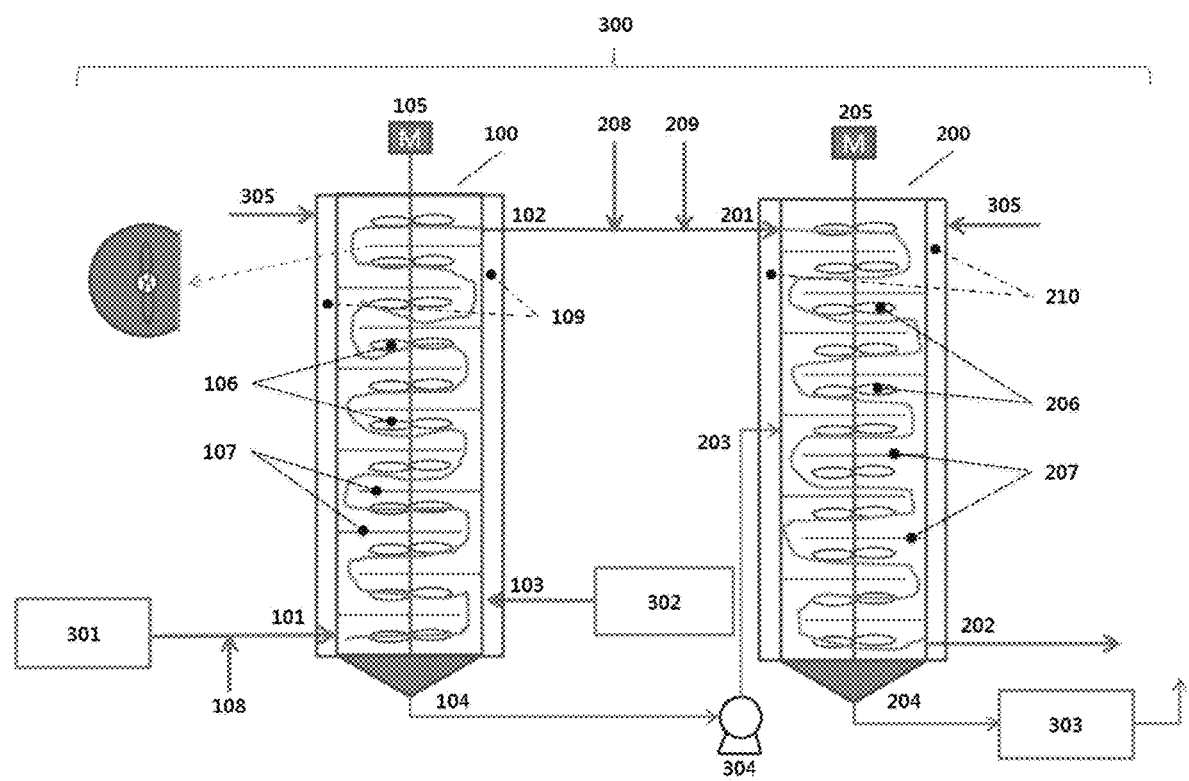

US 10,787,637 B2

CONTINUOUS FERMENTER FOR SEQUENTIAL FERMENTATION OF HEXOSE-PENTOSE

CROSS-REFERENCE TO RELATED APPLICATION

This application claims priority to Korean Patent Application No. 10-2015-0162793 filed Nov. 19, 2015, the disclosure of which is hereby incorporated in its entirety by reference.

TECHNICAL FIELD

The present disclosure relates to a continuous fermenter for sequential fermentation of hexose and pentose, and particularly, a continuous fermenter for sequential fermentation of hexose and pentose, characterized by including (a) a hexose fermenter equipped with a saccharified solution supply unit containing hexose, pentose and lignin, a plurality of trays closing at least half of the diameter of the fermenter, impellers disposed on each of the trays, an impeller driving unit, a lignin discharge unit disposed at the bottom of the fermenter, a fermented solution discharge unit, and a temperature control jacket; and (b) a pentose fermenter equipped with a fermented solution supply unit for supplying the fermented solution discharged from the hexose fermenter, a plurality of trays closing at least half of the diameter of the fermenter, impellers disposed on each of the trays, an impeller driving unit, a lignin discharge unit disposed at the bottom of the fermenter, a fermented solution discharge unit, and a temperature control jacket.

BACKGROUND ART

Biofuel is drawing attention as new alternative energy for replacing fossil energy on which mankind is currently entirely dependent. Further, there is a constantly increased demand for development of bio-based products produced from reproducible biomass.

At present, among biomass resources, bioethanol using sugar cane or corn as a raw material is actively prepared in the United States, Brazil, etc. This is because sugar cane or corn contains a lot of sucrose or starch, and it is easy to prepare a sugar solution therefrom and ferment it. However, sugar cane or corn is originally food, and in the case of using them as a raw material, there is a serious problem in that competition with food or feed occurs to cause a rise of raw material price. Thus, a technique for using non-edible biomass as a raw material is currently developed.

The non-edible biomass includes lignocellulosic biomass, and this may be utilized as an easily storable and transportable energy source or heat source such as bioethanol and biobutanol which may replace oil energy, and also its research value as a material for producing alternative chemical raw materials of petroleum products such as plastics is increasing. However, for economical mass production of various biochemicals and biomaterials by microbial fermentation from biomass, a technique capable of economical mass production of fermented sugar such as hexose and pentose is required.

Lignocellulosic biomass is composed of three main constituents of cellulose, hemicellulose and lignin, of which cellulose and hemicellulose are carbohydrates and may be converted to high value-added products through microbial fermentation after undergoing a saccharification process using an enzyme or acid. Further, a process for producing chemical products, bioenergy, etc. from lignocellulosic biomass may be divided into (i) pretreatment for removing the constituents inhibiting the reaction of the enzyme and microorganisms, and improving accessibility of the enzyme to cellulose and hemicellulose, (ii) enzymatic saccharification of converting cellulose and hemicellulose into fermentable saccharides by enzymatic hydrolysis, and (iii) microbial fermentation of converting the thus-produced sugars into a product using yeast, bacteria, and the like.

In particular, in the case of using a batch fermenter in the microbial fermentation, fermentation time is long, and thus, several fermenters should be installed for implementing a continuous operation, and due to the universal characteristic of fermentation strains, pentose is consumed after hexose is consumed, in which there is a difference in each fermentation condition. Further, in the case of batch fermentation, residual lignin after saccharification is also contained in the fermenter together, which inhibits the contact of the strains with sugar to cause long fermentation time and a high energy cost for agitation.

Korean Patent Publication No. 1261560 discloses a continuous saccharification fermenter of a device for preparing fermentable sugars, however, there is a difficulty in satisfying the fermentation condition of each sugar since one saccharification fermenter is used.

Thus, the present inventors exerts all possible efforts in order to develop a fermentation system capable of minimizing residual sugars after fermentation by differentiating the optimal fermentation condition of strains, through separated fermentation of hexose and pentose, and as a result, have developed a fermentation system, in which a bottom-up hexose fermenter and a top-down pentose fermenter are installed separately, and trays closing at least half of the diameter of the fermenter are disposed within each fermenter. As a result of supplying and fermenting a lignin-containing saccharified solution using the fermentation system, it was confirmed that the fermentation productivity was improved, thereby completing the present disclosure.

DISCLOSURE OF INVENTION

The present disclosure is directed to providing a continuous fermenter for sequential fermentation of hexose and pentose having an improved fermentation productivity, using a fermentation system in which a hexose fermenter and a pentose fermenter are separately installed, and trays closing at least half of the diameter of the fermenter are disposed within each fermenter.

In addition, a method of preparing useful materials is provided by sequential fermentation of hexose and pentose using the continuous fermenter.

An exemplary embodiment of the present disclosure provides a continuous fermenter for sequential fermentation of hexose and pentose, comprising: (a) a hexose fermenter equipped with: (i) a supply unit for a saccharified solution containing hexose, pentose and lignin; (ii) a plurality of trays closing at least half of a diameter of the hexose fermenter; (iii) impellers disposed on each of the trays; (iv) an impeller driving unit; (v) a lignin discharge unit disposed at a bottom of the hexose fermenter; and (vi) a fermented solution discharge unit; and (vii) a temperature control jacket; and (b) a pentose fermenter equipped with: (i) a fermented solution supply unit for supplying a fermented solution discharged from the hexose fermenter; (ii) a plurality of trays closing at least half of a diameter of the pentose fermenter; (iii) impellers disposed on each tray; (iv) an impeller driving unit; (v) a lignin discharge unit disposed at a bottom of the pentose fermenter; (vi) a fermented solution discharge unit; and (vii) a temperature control jacket.

Another embodiment of the present disclosure provides a method of preparing useful materials by sequential fermentation of hexose and pentose using the continuous fermenter.

BRIEF DESCRIPTION OF THE DRAWINGS

FIG. 1 is a schematic view of a continuous fermenter according to an exemplary embodiment of the present disclosure.

DETAILED DESCRIPTION OF MAIN ELEMENTS

100: Hexose fermenter
200: Pentose fermenter
300: Continuous fermenter
101: Saccharified solution supply unit
201: Fermented solution supply unit
301: Saccharification reactor
102: Fermented solution discharge unit
202: Fermented solution discharge unit
302: Seed fermenter
103: Strain supply unit
203: Lignin supply unit
303: Lignin separator
104: Lignin discharge unit
204: Lignin discharge unit
105: Impeller driving unit
205: Impeller driving unit
106: Impellers
206: Impellers
107: Trays
207: Trays
108: pH adjusting agent supply unit
208: Pentose supply unit
109: Temperature control jacket
209: pH adjusting agent supply unit
210: Temperature control jacket
305: Temperature control materials

BEST MODE FOR CARRYING OUT THE INVENTION

The present disclosure may be all achieved by the following description. The following description should be understood as describing preferred specific embodiments of the present disclosure, and the present disclosure is not necessarily limited thereto. Further, the accompanying drawing is for better understanding, and the present disclosure is not limited thereto. Details on the individual elements may be understood properly by the spirit detailed in the following related description.

Unless otherwise defined, all technical and scientific terms used herein have the same meaning as commonly understood by a person skilled in the art to which the present disclosure pertains. In general, the terminology used herein is well-known in the art and commonly used.

In the case of using a batch fermenter in the microbial fermentation, fermentation time is long, and thus, several fermenters should be installed for implementing a continuous operation, and due to the universal characteristic of fermentation strains, pentose is consumed after hexose is consumed, in which there is a difference in each fermentation condition. Further, in the case of batch fermentation, residual lignin after saccharification is also contained in the fermenter together, which inhibits the contact of the strain with sugar to cause long fermentation time and a high energy cost for agitation.

In the present disclosure, in order to develop a fermentation system capable of minimizing residual sugars after fermentation by differentiating the optimal fermentation condition of strains, through separated fermentation of hexose and pentose, a fermentation system in which a bottom-up hexose fermenter and a top-down pentose fermenter are installed separately, and trays closing at least half of the diameter of the fermenter, as illustrated in FIG. 1, are disposed within each fermenter has been developed. As a result of supplying and fermenting a lignin-containing saccharified solution using the fermentation system, it was confirmed that the fermentation productivity was improved.

Therefore, as an exemplary embodiment of the present disclosure, a continuous fermenter for sequential fermentation of hexose and pentose, comprising: (a) a hexose fermenter equipped with: (i) a supply unit for a saccharified solution containing hexose, pentose and lignin; (ii) a plurality of trays closing at least half of a diameter of the hexose fermenter; (iii) impellers disposed on each of the trays; (iv) an impeller driving unit; (v) a lignin discharge unit disposed at a bottom of the hexose fermenter; and (vi) a fermented solution discharge unit; and (vii) a temperature control jacket; and (b) a pentose fermenter equipped with: (i) a fermented solution supply unit for supplying a fermented solution discharged from the hexose fermenter; (ii) a plurality of trays closing at least half of a diameter of the pentose fermenter; (iii) impellers disposed on each tray; (iv) an impeller driving unit; (v) a lignin discharge unit disposed at a bottom of the pentose fermenter; (vi) a fermented solution discharge unit; and (vii) a temperature control jacket, is provided.

More specifically, in the present disclosure, it is preferred that the saccharified solution containing hexose, pentose and lignin is supplied to the bottom of the hexose fermenter, in which lignin in the saccharified solution sinks to the bottom of the fermenter so that it is present in a solid state only in the lower tray, thereby improving the fermentation speed at the top of the fermenter.

In the present disclosure, the hexose fermenter is a bottom-up fermenter, in which a plurality trays closing at least half of the diameter of the fermenter are installed alternately at a regular distance, and it is preferred that the number of trays is 10-60, and the distance between the trays is 0.5-1 m, considering the equipment height in the commercial plant is at most 20-30 m. It is preferred that the length to diameter ratio (L/D) of the fermenter is 2 or more, considering that the load of the driving unit increases with the increase of the diameter of the impeller. The reason why the tray occludes at least half of the diameter of the fermenter is because the saccharified solution is prevented from directly going up from bottom to top of the fermenter, thereby increasing the contact time of the saccharified solution and strains to shorten the fermentation time, and allowing unwanted lignin for fermentation to be precipitated to be discharged to the bottom through the opening of the trays by impellers. The distance between the trays and the size of the trays may be designed depending on the throughput, the contents of hexose and pentose in the saccharified solution, and the fermentation speed of the strains.

In the present disclosure, the impeller is disposed on the tray installed within the hexose fermenter, and it is preferred that the impeller is installed closely to the upper part of each tray, so that the lignin precipitated on the upper part of the tray is pushed to an empty space to fall down to the bottom of the fermenter. The distance between the tray and the impeller being 1-10 mm is effective for removing the lignin. In addition, the distribution degree of the strains may be controlled by adjusting the speed by the impeller driving unit. In the case that the rotational speed of the impeller by the impeller driving unit is low, the proper contact of the saccharified solution and the strains may be difficult, and in the case of being high, the lignin may not be precipitated on the tray and move upwardly together with the saccharified solution, thereby rather inhibiting the contact of the saccharified solution and the strain. Thus, it is preferred to operate the impellers at 5-60 rpm. The impeller rotational speed may be determined by several factors such as the supply amount of the saccharified solution and the content of the lignin. Besides, a unit for further supplying a pH adjusting agent to the supply unit of the saccharified solution discharged from the saccharification reactor may be included, and the pH adjusting agent may be weak acid/strong acid, or weak base/strong base. The reason why the pH adjusting agent is added like this is because the pH conditions at the time of saccharification and hexose fermentation are different from each other. In addition, in order to maintain the optimal activity of the fermentation strains, the temperature of the hexose fermenter may be constantly maintained, which is performed by installing a jacket. The temperature control materials supplied to the jacket may be electric or steam or cooling water.

In the present disclosure, it is preferred that the fermented solution discharged from the hexose fermenter is supplied to the top of the pentose fermenter, and the fermented solution contains the product from the hexose fermenter, pentose and strains. In addition, a unit for further supplying pentose to the supply unit of the fermented solution discharged from the hexose fermenter may be included, and the pentose may be produced by a monomerization reaction of pentose oligomer present in a pretreated liquid, and for example, may be xylose, ribose or arabinose produced from decomposition of the oligomer derived from hemicellulose. Besides, a unit for further supplying a pH adjusting agent to the supply unit of the fermented solution discharged from the hexose fermenter may be included, and the pH adjusting agent may be weak acid/strong acid, or weak base/strong base. The reason why the pH adjusting agent is added like this is because the pH conditions at the time of hexose fermentation and pentose fermentation by strains may be different from each other, or when there is a pH change by the hexose fermentation product, the pH should be adjusted.

In addition, in order to maintain the optimal activity of the fermented strains, the temperature of the pentose fermenter may be constantly maintained, which is performed by installing a jacket. The temperature control materials supplied to the jacket may be electric or steam or cooling water.

In the present disclosure, the pentose fermenter is a top-down fermenter, and the constitutions of the trays, impellers and impeller driving unit within the fermenter are identical to those of the hexose fermenter, but the number of the trays and impellers to be installed may be varied with the size of the fermenter.

In the present disclosure, it is preferred to further include a unit for supplying the lignin discharged from the lignin discharge unit disposed at the bottom of the hexose fermenter to the middle of the pentose fermenter, and since the lignin discharged to the bottom of the hexose fermenter contains sugars, the sugars are supplied to the middle of the pentose fermenter to be converted to a useful material as a whole, which may be carried out by a lignin transfer pump.

In the present disclosure, it is preferred to further include a unit for separating the lignin discharged from the lignin discharge unit disposed at the bottom of the pentose fermenter. Typically, a lignin separator which is commercially widely used may be used.

In the present disclosure, in the case that the sizes of the hexose fermenter and the pentose fermenter are differently designed considering the fermentation speed thereof, fermentation efficiency may be increased, and investment costs may be reduced. Besides, the fermentation speed of the hexose fermenter may be controlled by adjusting the supply speed of the saccharified solution supply unit and the fermentation speed and the amount of the residual sugars of the pentose fermenter may be controlled by adjusting the discharge speed of the fermented solution discharge unit. Further, the operation conditions such as the temperature and pH of the hexose fermenter and the pentose fermenter may be controlled, thereby improving fermentation performance, and increasing the fermentation efficiency, and thus, shortening the fermentation time.

Hereinafter, the present disclosure will be described with reference to the accompanying drawing.

FIG. 1 is a schematic diagram of the continuous fermenter 300 according to an exemplary embodiment, in which a saccharified solution discharged from a saccharification reactor 301 is supplied to a saccharified solution supply unit 101 at the bottom of a hexose fermenter 100, and strains are supplied from a seed fermenter 302 to the hexose fermenter by a strain supply unit 103. Here, the saccharified solution supplied to the hexose fermenter 100 is supplied to the bottom of the fermenter, so that most of lignin in a solid state sinks to the bottom of the fermenter. In addition, impellers 106 are driven by an impeller driving unit 105, and installed closely to the upper part of trays 107 so that the lignin precipitated on the trays 107 installed at a regular distance may fall down to the bottom of the fermenter. In order to maintain the optimal operation condition of hexose fermentation, a pH adjusting agent supply unit 108 and a jacket for adjusting temperature 109 are installed. A fermentation product from the hexose fermenter, and a fermented solution containing pentose and strains are discharged from the hexose fermenter through a discharge unit 102, and supplied to a fermented solution supply unit 201 at the top of the pentose fermenter 200. To the fermented solution supply unit, a pentose supply unit 208 or a pH adjusting agent supply unit 209 may be added, if necessary. An impeller driving unit 205, impellers 206, and trays 207 in the pentose fermenter are configured identically to those in the hexose fermenter, and the lignin discharged by a lignin discharge unit 104 at the bottom of the hexose fermenter is supplied to a lignin supply unit 203 in the middle of the pentose fermenter by a lignin pump 304 to ferment the sugars partially contained in the lignin. A jacket 201 is installed in order to maintain the temperature of the pentose fermenter constant. Finally, the fermentation product from the hexose fermenter and the fermentation product from the pentose fermenter are discharged by a fermented solution discharge unit 202, and the lignin discharged by a lignin discharge unit 204 at the bottom of the pentose fermenter may be separated through a lignin separator 303.

Another embodiment of the present disclosure relates to a method of preparing useful materials by sequential fermentation of hexose and pentose using the continuous fermenter.

More specifically, it is preferred that the hexose of the present disclosure includes one or more sugars selected from the group consisting of glucose, galactose and mannose, and the pentose includes one or more sugars selected from the group consisting of xylose, ribose and arabinose.

In the present disclosure, the useful material may be ethanol, propanol, butanol, pentanol, hexanol, butadiene or a mixture thereof, but not limited thereto.

In the present disclosure, it is preferred that the saccharified solution containing hexose, pentose and lignin is supplied to the bottom of the hexose fermenter, in which lignin in the saccharified solution sinks to the bottom of the fermenter so that it is present in a solid state only in the lower tray, thereby improving the fermentation speed at the top of the fermenter.

In the present disclosure, it is preferred that the fermented solution discharged from the hexose fermenter is supplied to the top of the pentose fermenter, and the fermented solution contains the product from the hexose fermenter, pentose and strains. In addition, a unit for further supplying pentose to the supply unit of the fermented solution discharged from the hexose fermenter may be included, and the pentose may be produced by a monomerization reaction of pentose oligomer present in a pretreated liquid, and a unit for further supplying a pH adjusting agent to a fermented solution supply unit for supplying the fermented solution discharged from the hexose fermenter may be included.

In the present disclosure, it is preferred to further include a unit for supplying the lignin discharged from the lignin discharge unit disposed at the bottom of the hexose fermenter to the middle of the pentose fermenter, and since the lignin discharged to the bottom of the hexose fermenter contains sugars, the sugars are supplied to the middle of the pentose fermenter to be converted to a useful material as a whole, which may be carried out by a lignin transfer pump.

In the present disclosure, it is preferred to further include a unit for separating the lignin discharged from the lignin discharge unit disposed at the bottom of the pentose fermenter.

In the present disclosure, 'fermentation' is performed by adding yeast, *Clostridium*, *Escherichia coli*, and all other microorganisms capable of producing useful materials to the fermenter, and the kind of the produced useful materials is dependent on the kind of added specific microorganism at the time of fermentation.

In the present disclosure, the strain producing the useful material may include all microorganisms capable of producing useful materials by fermenting a carbon source. For example, the microorganism may be selected from the group consisting of a *Clostridium* genus strain, a *Pseudomonas* genus strain, a *Rhizopus* genus strain, An *Aspergillus* genus strain, a *Corynebacterium* genus strain, an *Actinobacillus* genus strain, yeast, a *Candida* yeast, a *Pichia* yeast, *E. Coli*, and lactic acid bacteria, and more specifically, may include *C. tyrobutyricum, C. butyricum, C. acetobutyricum, P. aeruginosa, P. putida, P. fluorescens, R. arrhizus, R. oryzae, A. oryzae, C. glutamicum* and *L. Acidophilus*, but not limited thereto.

In the present disclosure, the 'useful materials' may be amino acids, biopolymers, biofuels, biochemicals, specialty chemicals, various enzymes, and the like, and are not limited thereto, as long as they may be obtained from microorganism fermentation.

Lignocellulosic biomass are, though the composition and content of the chemical component forming wood are varied with softwood and hardwood, and the species and age of trees, generally mainly composed of cellulose, hemicellulose and lignin, and thus, it is also commonly called lignocellulose, and since it contains polysaccharide cellulose which is the main component of a woody or herbaceous biomass cell wall, it is also called cellulosic biomass.

Therefore, the 'biomass' of the present disclosure may be used interchangeably with cellulosic biomass, woody biomass, lignocellulosic biomass, and lignum biomass.

The biomass according to the present disclosure may include biomass derived from crops such as grains and starch containing refined starch; for example, stem, bagasse and straw from rice, wheat, rye, oats, barley, rapeseed and sugarcane; for example, needle leaf trees of Pinussylvestris, *Pinus* radiate; for example, broad leaf trees of *Alix* spp., *Eucalyptus* spp.; for example, tubers such as beet and potato; for example, cereals of rice, wheat, rye, oats, barley, rapeseed, sugarcane and corn, or the like.

INDUSTRIAL APPLICABILITY

The continuous fermenter for sequential fermentation of hexose and pentose according to the present disclosure may minimize residual sugars after fermentation by differentiating the optimal condition of strains through separated fermentation of hexose and pentose. In addition, lignin is separated before fermentation to increase contact of strains and sugars, thereby shortening fermentation time, through which productivity is improved, and the size of the equipment may be small as compared with that having the same capacity, thereby reducing investment costs. Further, continuous operation is possible, and thus, an economic effect from the reduction of the number of used equipment, and significant reduction of the area occupied by the equipment as compared with the conventional batch fermenter is very large.

The present disclosure has been described in detail in specific parts, and it is obvious that such specific technique is only a preferred exemplary embodiment to a person skilled in the art, without limiting the scope of the present disclosure. Thus, the substantial scope of the present disclosure will be defined by the appended claims and their equivalents.

What is claimed is:

1. A method of preparing a useful material by sequential fermentation of hexose and pentose comprising the steps of:
    (a) supplying a saccharified solution containing hexose, pentose, and lignin to a bottom-up hexose fermenter equipped with:
        (i) a supply unit for the saccharified solution containing hexose, pentose, and lignin;
        (ii) a plurality of trays closing at least half of a diameter of the hexose fermenter, wherein the plurality of trays are installed alternately and at a regular distance, wherein the number of trays is 10-60, and wherein the distance between trays is 0.5-1 m;
        (iii) impellers disposed on each of the trays;
        (iv) an impeller driving unit;
        (v) a lignin discharge unit disposed at a bottom of the hexose fermenter;
        (vi) a fermented solution discharge unit; and
        (vii) a temperature control jacket;
    (b) supplying a fermented solution discharged from the hexose fermenter to a top-down pentose fermenter equipped with:
        (i) a fermented solution supply unit for supplying a fermented solution discharged from the hexose fermenter;
        (ii) a plurality of trays closing at least half of a diameter of the pentose fermenter, wherein the plurality of trays are installed alternately and at a regular distance, wherein the number of trays is 10-60, and wherein the distance between trays is 0.5-1 m;
(iii) impellers disposed on each tray;
(iv) an impeller driving unit;
(v) a lignin discharge unit disposed at a bottom of the pentose fermenter;
(vi) a fermented solution discharge unit;
(vii) a temperature control jacket; and
(viii) a lignin and pentose supply unit for supplying lignin and pentose discharged from the lignin discharge unit disposed at the bottom of the hexose fermenter to a middle of the pentose fermenter; and (c) recovering the useful material, wherein pentose is supplied to a top of the top-down pentose fermenter through the fermented solution supply unit and to the middle of the top-down pentose fermenter through the lignin and pentose supply unit.

2. The method of claim 1, wherein the hexose is glucose and the pentose is xylose.

3. The method of claim 1, wherein the useful material is ethanol.

4. The method of claim 1, wherein the saccharified solution containing hexose, pentose, and lignin is supplied to the bottom of the hexose fermenter.

5. The method of claim 1, wherein the pentose fermenter further comprises a unit for supplying pentose to the fermented solution supply unit for supplying the fermented solution discharged from the hexose fermenter.

6. The method of claim 1, wherein the pentose fermenter further comprises a unit for separating a lignin discharged from the lignin discharge unit disposed at the bottom of the pentose fermenter.

\* \* \* \* \*